(12) United States Patent
Kusch et al.

(10) Patent No.: US 9,797,790 B2
(45) Date of Patent: Oct. 24, 2017

(54) MEDICAL EXAMINATION AND/OR TREATMENT DEVICE

(71) Applicants: Robin Kusch, Bayreuth (DE); Stefan Sattler, Forchheim (DE); Stefan Schuster, Forchheim (DE)

(72) Inventors: Robin Kusch, Bayreuth (DE); Stefan Sattler, Forchheim (DE); Stefan Schuster, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 14/949,816

(22) Filed: Nov. 23, 2015

(65) Prior Publication Data

US 2016/0166325 A1    Jun. 16, 2016

(30) Foreign Application Priority Data

Nov. 24, 2014   (DE) .................... 20 2014 009 315 U (51) Int. Cl.
| | |
|---|---|
| *G01N 3/08* | (2006.01) |
| *G01L 5/00* | (2006.01) |
| *A61B 6/10* | (2006.01) |
| *A61B 19/00* | (2006.01) |
| *A61B 6/00* | (2006.01) |
| *A61B 90/00* | (2016.01) |

(52) U.S. Cl.
CPC ............ *G01L 5/0052* (2013.01); *A61B 6/102* (2013.01); *A61B 19/46* (2013.01); *A61B 6/4441* (2013.01); *A61B 2019/465* (2013.01); *A61B 2090/064* (2016.02)

(58) Field of Classification Search
CPC .. G01N 3/08; G01N 3/36; G01N 3/32; G01N 3/30; G01L 5/0052; A61B 6/102; A61B 19/46; A61B 2090/064; G01B 5/30; G01M 7/08; G01M 17/04; B25D 9/005
USPC ...... 73/818, 788, 790, 813, 760, 808, 12.09, 73/12.01, 11.01, 11.04
See application file for complete search history.

(56) References Cited

U.S. PATENT DOCUMENTS

| | | | |
|---|---|---|---|
| 5,570,770 A | 11/1996 | Baaten et al. | |
| 6,550,964 B2* | 4/2003 | Guerit | G01N 23/04 378/189 |
| 2009/0038073 A1* | 2/2009 | Dippl | A61G 13/06 5/611 |

(Continued)

FOREIGN PATENT DOCUMENTS

| | | |
|---|---|---|
| DE | 9403972 U1 | 7/1994 |
| DE | 102012100404 A1 | 7/2013 |
| EP | 0301198 B1 | 7/1993 |

*Primary Examiner* — Lisa Caputo
*Assistant Examiner* — Nigel Plumb
(74) *Attorney, Agent, or Firm* — Lempia Summerfield Katz LLC (57) ABSTRACT

A medical examination, treatment, or examination and treatment device is provided. The medical examination, treatment, or examination and treatment device includes a cover panel. The cover panel includes a sensor for detecting a collision. The sensor includes a first plate mounted on the examination, treatment, or examination and treatment device, and a second plate mounted on the inside of the cover panel and spaced apart from the first plate. Spring elements are disposed between the first plate and the second plate.

18 Claims, 5 Drawing Sheets

(56) References Cited

U.S. PATENT DOCUMENTS

| | | | |
|---|---|---|---|
| 2012/0236999 A1* | 9/2012 | Altvater | A61B 6/4441 378/196 |
| 2013/0083894 A1* | 4/2013 | Niebler | A61B 6/4441 378/62 |
| 2014/0102217 A1* | 4/2014 | Inaba | G01L 1/10 73/862.59 |

* cited by examiner

MEDICAL EXAMINATION AND/OR TREATMENT DEVICE

This application claims the benefit of DE 20 2014 009 315.6, filed on Nov. 24, 2014, which is hereby incorporated by reference in its entirety.

BACKGROUND

The present embodiments relate to a medical examination and/or treatment device on which at least one cover panel having at least one sensor for detecting a collision is mounted.

Diagnostic and interventional systems used for angiography, cardiology, neurology, or hybrid OPs often have a C-arm as a support for system parts used for imaging. A C-arm is mostly movable in a multiaxial motorized manner and may perform three-dimensional movements in space. Such devices are controlled either by an operator, or alternatively, system parts such as a C-arm may also be moved semi-automatically or in an automated manner. For example, a C-arm may be moved along a trajectory around a patient (e.g., in order to acquire reconstruction images required for a 3D scan).

In recent years, examination and/or treatment devices with support systems for the C-arm that are based on industrial robotics technology have been developed. Modern multi-axis designs are characterized by an increased range of movement, but this has also entailed heightened safety requirements for an examination and/or treatment device of this kind. In order to prevent a collision of moving parts (e.g., of a C-arm) with non-moving parts or with the patient, sensors are incorporated in the examination and/or treatment device. Corresponding standards and regulations in which safety requirements are defined exist both for robots and for medical devices.

Even if a collision is detected by a sensor, in the event of a collision and after disconnection of a drive, a force- and mass-dependent overtavel is still present because of the mass inertia of the system. The cover panel of conventional examination and/or treatment devices is therefore of mechanically compliant design so that defined forces exerted in the event of a collision with a patient are not exceeded. Such a cover panel of an examination and/or treatment device may also include a plurality of panel elements.

In the prior art, different collision protection devices have already been proposed. EP 0 301 198 A1 discloses a medical safety device configured to prevent the patient's body from being subjected to excessive contact pressure of a component of a diagnostic and/or treatment device. For this purpose, an elastically deformable element that is filled with a liquid or gas and has a pressure sensor is provided. In the event of contact of the elastic element with the patient's body, a drive of the patient table is disconnected via a switch.

DE 10 2012 100 404 A1 discloses collision protection for a medical device. This document proposes to provide a medical device body with a collision detection component including an array of sensors. The pressure sensors are disposed between a base body or housing of the medical device and an outer shell including an elastically deformable and/or elastically compressible material.

Although conventional collision protection devices of this kind provide a high degree of protection from accidental collisions between a component of a medical examination and/or treatment device and a patient, in practice, it is difficult to equip a medical examination and/or treatment device therewith over a wide area. Cover panel members having a complex shape make it difficult to incorporate collision protection. In most cases, a central collision sensor system is no longer possible, and it is difficult to adhere precisely to defined adjustment and overrun paths. In addition, conventional systems having switching elements and spring-mounted panel parts are characterized by a complex housing geometry and a complicated, costly, and mechanically vulnerable substructure. The high degree of constructional complexity results primarily from the precise adherence to the required adjustment and overrun paths in all directions in the case of panel parts having complex geometries.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a medical examination and/or treatment device having a collision protection device that may be implemented simply and inexpensively even in the case of cover panel members of complex shape is provided.

In one embodiment of a medical examination and/or treatment device, a sensor has a first plate mounted on the examination and/or treatment device and a second plate mounted on the inside of the cover panel and spaced apart from the first plate. Spring elements are disposed between the two plates.

The provided special spring elements allow flexible attachment of panel parts to a base body of the medical examination and/or treatment device, and allow reliable detection of a collision by the sensor. The spring elements provide mechanical damping of impacts or collisions, while at the same time the collision may be detected by the integrated sensor and the drive of the collision-causing drive disconnected.

For the examination and/or treatment device according to one or more of the present embodiments, the spring elements are made of a spring wire material or an elastomer. Spring elements made of a spring wire material are mainly used, but in certain cases, spring elements made of an elastomer may be used. In addition, a combination of both variants may also be used.

Particularly reliable operation is achieved if the spring elements are at least approximately semicircular and form a ring with the two plates. A ring-shaped spring element of this kind is particularly well able to absorb an external force and damp the external force by deformation.

For the medical examination and/or treatment device of one or more of the present embodiments, a modular insert having at least one component is disposed on one of the two plates. The at least one component includes a switching element, a gyrosensor, an elastically deformable building block, a hemispherically shaped building block, a building block made of metal or a metal alloy, a piezoelectric element, or any combination thereof. The modular insert may therefore be assembled by selecting one or more components from this group and combining the one or more components to form the modular insert. A modular insert may therefore be flexibly assembled for a desired characteristic or a required function. For this purpose, the different components undertake different tasks or functions. Using a switching element, an external force or a torque may be detected if a switching contact is triggered thereby. An acceleration, a velocity or a position in three-dimensional space may be detected by a gyrosensor. An elastically deformable building block is used as a damper in the event of a collision. A hemispherically shaped building block that may form the nonattached end of a modular insert is not only able to absorb forces acting in the longitudinal direction and therefore axially, but a hemispherically shaped building block may also absorb or detect transverse forces or torques. A building block made of metal or a metal alloy may be used as a stop or end stop to limit a movement. A piezoelectric element may be used as a force sensor.

A further development of the medical examination and/or treatment device according to one or more of the present embodiments provides that the components of the modular insert are of columnar design and extend from one plate to the other plate. The first and second plate may be disposed parallel to one another. The modular insert is disposed on one plate, pointing toward the other plate.

In this way, a modular insert of the medical examination and/or treatment device is assembled from building blocks selected from the mentioned components of the group depending on the respective requirements. The specific setup and selection of the individual components is determined by the desired characteristics and functions.

According to a further development, the sensor may include at least two modular inserts spaced apart from one another. The two modular inserts may be disposed side by side on the same plate. Each modular insert may have a hemispherically shaped component as the nonattached end. This enables external torques to be limited.

An alternative variant provides that a modular insert is provided with a limiting element disposed on the opposite plate. The limiting element may be implemented as a hollow cylinder. The limiting element prevents lateral displacement of the two plates relative to one another, as well as also limiting an applied torque to a particular value. As mentioned, the limiting element may be implemented as a hollow cylinder, and may likewise include a plurality of parallel bars.

In one embodiment, one of the two plates includes a multiaxial force sensor or is implemented as a multiaxial force sensor. Accordingly, a force sensor may be mounted on a plate. Alternatively, a force sensor may also be made plate-shaped. In this context, the multiaxial force sensor may be disposed between two spring elements disposed on opposite sides of the force sensor. For example, this enables displacement of a cover panel to be limited.

A further development may provide that one of the two plates has a switching element such as a pushbutton. The pushbutton is actuated by a collision so that the pushbutton generates a switching signal, in response to which a drive for a moving component such as a C-arm, for example, may be disconnected.

In one embodiment, the first plate and the second plate of the medical examination and/or treatment devices are electrically conductive, and at least one plate has at least one contact element extending to the other plate. In this configuration, the spring elements mounted between the plates may be electrically nonconducting.

In one embodiment, the medical examination and/or treatment device has a multiaxially movable boom with a C-arm. The cover panel of the C-arm has the at least one sensor.

DETAILED DESCRIPTION

Figure 1:
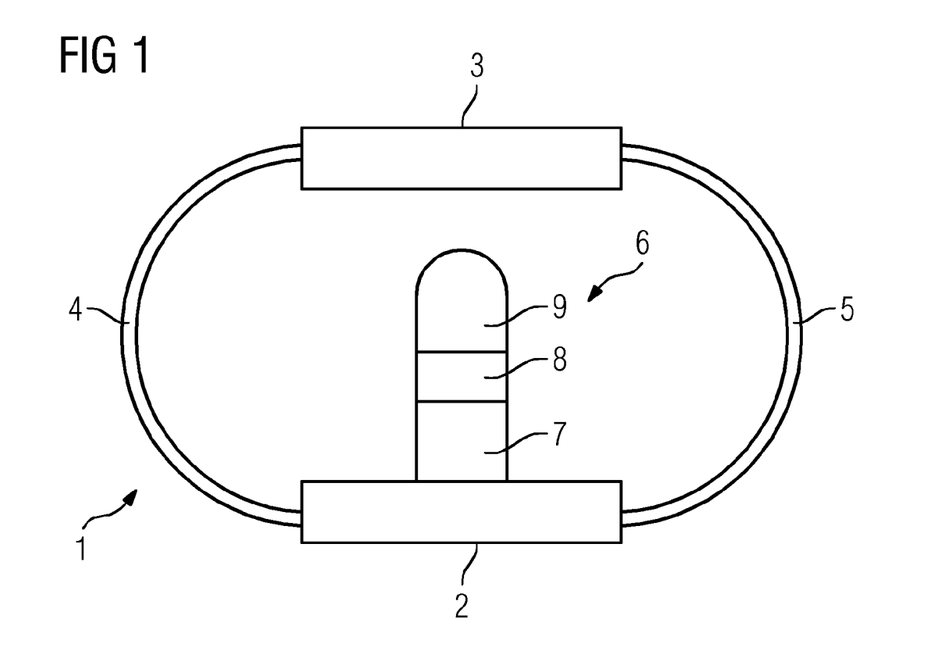
FIG. 1 schematically illustrates an exemplary embodiment of a sensor for a medical examination and/or treatment device.

FIG. 1 shows a sensor 1 that may be configured to detect a collision and to be disposed on a cover panel of a medical examination and/or treatment device. The sensor 1 includes a first plate 2 that, in the mounted state, is disposed on the outside of a body of the examination and/or treatment device. The sensor 1 also includes a second plate 3 that is spaced apart from the first plate 2 and disposed parallel thereto. The second plate 3, in the mounted state, is disposed on the inside of a cover panel or cover panel member of the medical examination and/or treatment device. Disposed between the two plates 2, 3 are spring elements 4, 5 that are curved in a circular-segment-shaped manner and form a ring with the two plates 2, 3. The spring elements 4, 5 are implemented as wire spring elements so that the ring may be elastically deformed by a compressive force exerted on the plate 3.

FIG. 1 shows that a modular insert 6 that is located inside the ring and spaced apart from the opposite plate 3 is disposed on the plate 2. In the exemplary embodiment shown, the modular insert 6 includes three components. The first, lower component that is attached to the plate 2 is a building block 7 made of metal. The building block 7 is used to limit the spring deflection. Adjacent thereto is an elastic building block 8 that is seated on the building block 7. The elastic building block 8 includes an elastic material (e.g., a material having a much greater elasticity than the building block 7). In the exemplary embodiment shown, the building block 7 is made of steel, and the elastic building block 8 is made of an elastomer. When stress is applied, the elastic building block 8 deforms elastically. On top of the building block 8 is a hemispherically shaped building block 9 that causes torques applied via the second plate 3 to be able to continue to be exerted on contact with the elastic building block 8. An externally applied torque moves the second plate 3 under elastic deformation of the spring element 4, 5 against the hemispherically shaped building block 9, causing the elastic building block 8 to be deformed or compressed. This causes an intensification of the spring force in the longitudinal direction of the modular insert 6 before the spring deflection is limited.

Figure 2:
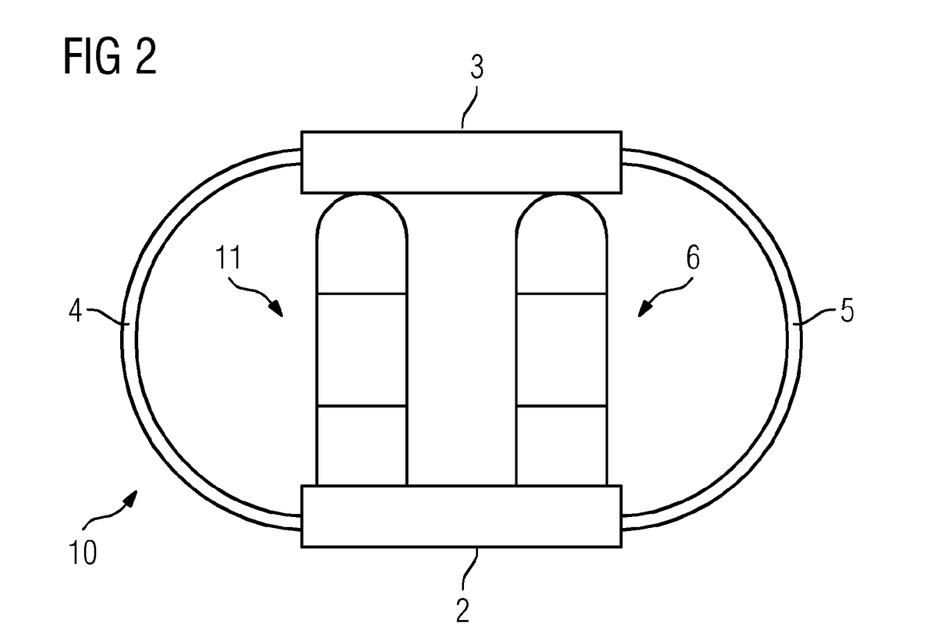
FIG. 2 schematically illustrates another exemplary embodiment of a sensor.

FIG. 2 is a similar exemplary embodiment to FIG. 1 and shows a sensor 10 that, as in the first exemplary embodiment, has a first plate 2 and a second plate 3 that form a ring with spring elements 4, 5. Unlike in the previous exemplary embodiment, the sensor 10 includes two modular inserts 6, 11 that are spaced apart from one another on the first plate 2.

In the exemplary embodiments shown in FIGS. 1 and 2, the spring force or spring stiffness for all six degrees of freedom may be influenced via the sizing, arrangement, and material selection of the spring elements 4, 5.

As a variant of the sensor 10 shown in FIG. 2, three modular inserts may also be used to limit torques acting about the horizontal and the vertical axis. For this purpose, three modular inserts that have comparatively large elastic building blocks are used to limit translational motion of the upper plate 3 vertically to the lower plate 2 as little as possible.

Figure 3:
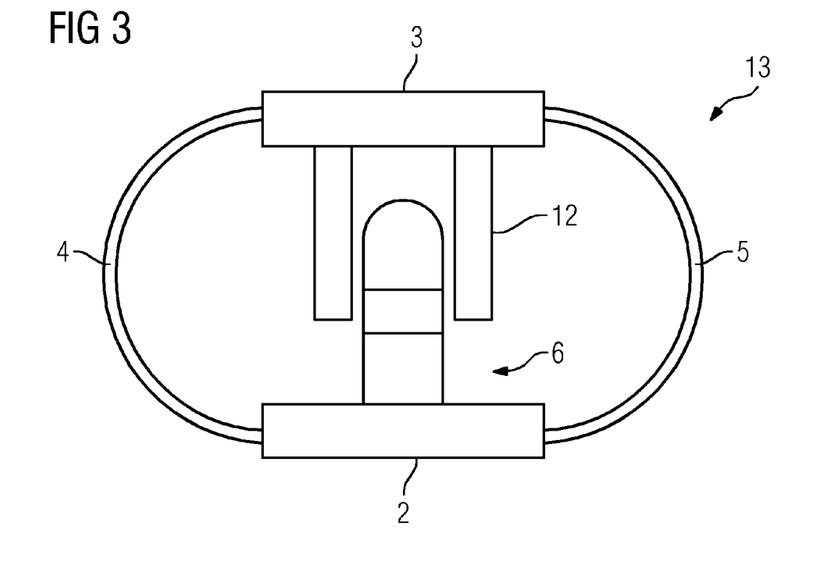
FIG. 3 schematically illustrates another exemplary embodiment of a sensor.

FIG. 3 is an exemplary embodiment of a sensor 13 of similar design to the sensor 1 shown in FIG. 1. Corresponding components will not therefore be described again in detail. In addition to the modular insert 6 that is disposed on the plate 2 between the plates 2, 3, a limiting element 12 configured as a hollow cylinder is present, which in FIG. 3, is disposed on the upper plate 3 and partially encloses the modular insert 6. Another limiting element that is disposed on the plate 2 and encloses the first limiting element 12 may also optionally be used. This limits an external torque and prevents lateral displacement of the two plates 2, 3. If a second limiting element is present, the plates 2, 3 may only be displaced vertically with respect to one another. Through the selection of an elastic building block in the first limiting element 12, possibly also in the other limiting element, a certain play or a desired progressive spring force characteristic may be produced. Coating of the hollow cylindrical limiting element 12 with an elastic material causes damping of other axes or degrees of freedom and also minimizes noise. In this way, controllable limiting of the travel in five degrees of freedom is achieved.

Figure 4:
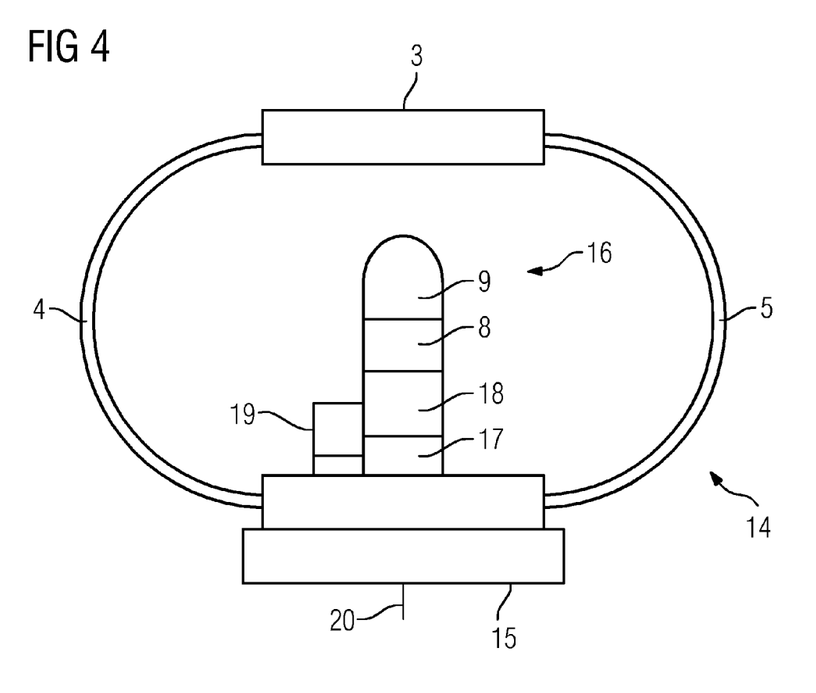
FIG. 4 schematically illustrates another exemplary embodiment of a sensor.

FIG. 4 is another exemplary embodiment and shows a sensor 14 of similar design to the sensor 1 shown in FIG. 1. The difference between FIG. 4 and FIG. 1 is that a first plate 15 is implemented as a multiaxial force sensor. In the exemplary embodiment shown, the multiaxial force sensor is a 6D force sensor that may therefore detect forces along three orthogonal axes and torques about three axes. A modular insert 16 includes a switching element 17, a gyrosensor 18, an elastic building block 8, and a hemispherically shaped building block 9 that are disposed in that sequence on the first plate 15, which is implemented as a multiaxial force sensor. The individual components of the modular insert 16 are provided with schematically represented conductors 19 that pass through the plate 15 and come together in a central output line 20.

Figure 5:
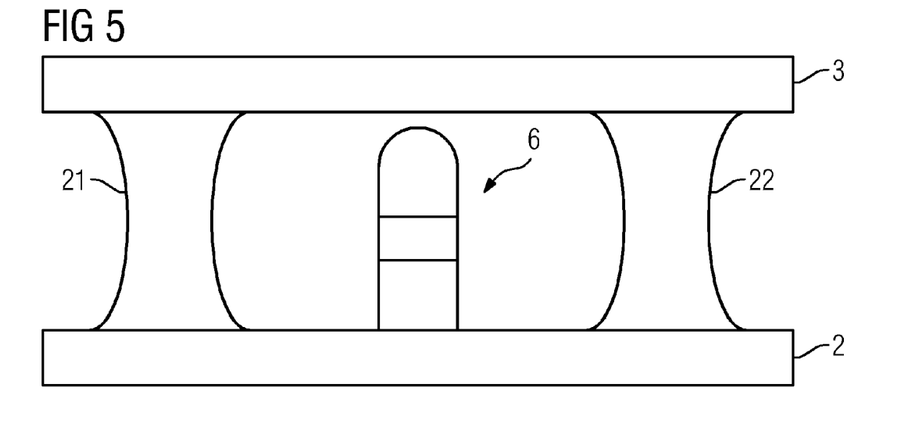
FIG. 5 schematically illustrates another exemplary embodiment of a sensor.

FIG. 5 shows another exemplary embodiment including a first plate 2, a second plate 3, and, disposed therebetween, spring elements that in this exemplary embodiment include an elastomeric material. The two spring elements 21, 22 possess a hyperboloidal shape. Because of the elastomeric material used, the spring elements 21, 22 also act as dampers. Disposed between two plates 2, 3 is a modular insert 6 that is attached to the lower plate 3 and spaced apart from the upper plate 2. In the event of an external force, the spring elements 21, 22 deform until the plate 3 touches the modular insert 6. The external force to be applied then increases, as not only the spring elements 21, 22 but also the elastic element of the modular insert 6 are to be compressed. The spring deflection may be influenced (e.g., controlled) by selecting elastic spring elements of different shape and thickness.

The spring elements described in the different exemplary embodiments allow a restoring force to be absorbed in three orthogonal directions, against any torques and with respect to a combination of forces and torques. By selecting a suitable spring force of the spring elements, a required range of movement of a panel part may be determined. Likewise, a restoring path for a switching element may be defined. By using an additional modular insert or a plurality of inserts, adaptation to particular applications may likewise take place. Solid building blocks (e.g., a metal building block) enable the spring deflection to be limited, whereas elastic elements such as the elastic building block 8 provide a certain adjustment path before the spring deflection is limited, while simultaneously increasing the spring force in this area. Additional loading of the spring in other directions remains unaffected thereby and is decelerated by the spring with a normal restoring force. A hemispherically shaped building block may react to an external torque in spite of a limitation in one direction. The spring elements and therefore the entire sensor may therefore be configured in a highly flexible manner for a required application. In addition, the modular inserts in a defined operating direction act as overload protection for other spring element based sensors present on the medical examination and treatment device.

Figure 6:
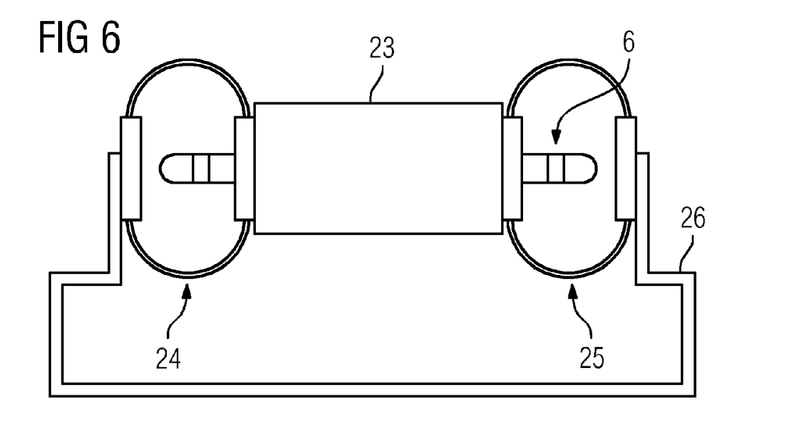
FIG. 6 schematically illustrates one embodiment of an arrangement including a force sensor that is disposed between two sensors.

FIG. 6 shows an exemplary embodiment in which a sensor (e.g., a force sensor 23) is disposed between two sensors 24, 25. The sensors 24, 25 are each identical to the sensor 1 shown in FIG. 1.

The sensors 24, 25 are disposed such that corresponding modular inserts 6 point from the force sensor 23 toward the respective opposite plate. On the outer side of the plates is a cover panel 26 of a medical examination and/or treatment device. The spring elements of the two sensors 24, 25 limit displacement only in the direction of the application of force. In the exemplary embodiment shown, a horizontally applied force is therefore limited. Tilting of the arrangement is possible, although the spring force of the spring elements of the sensors 24, 25 is then to be overcome.

Figure 7:
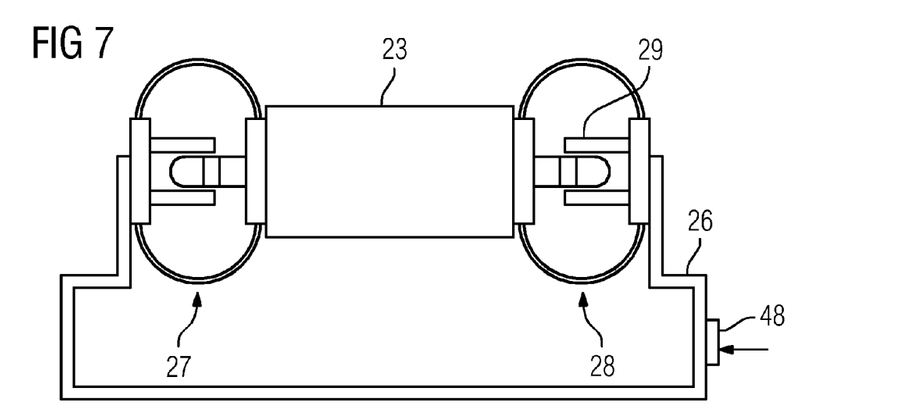
FIG. 7 schematically illustrates an example with an arrangement similar to FIG. 6.

FIG. 7 shows a similar exemplary embodiment to FIG. 6, where the force sensor 23 is disposed between two sensors 27, 28 that correspond in each case to the sensor 13 shown in FIG. 3. The sensors 27, 28 therefore each have, in addition to the arrangement shown in FIG. 6, a limiting element 29 implemented as a hollow cylinder. The limiting element 29 is located on the plate spaced apart from the force sensor 23. The two outer plates on which the limiting elements 29 are located are attached to the inside of the cover panel 26. In comparison to the arrangement shown FIG. 6, the limiting elements 29 additionally define the tilt of the sensor 27, 28, thereby also limiting the compliance perpendicular to the limiting elements 29.

The cover panel 26 is a component part of the C-arm and has a pushbutton 48. The cover panel 26 is attached to the force sensor 23 via the sensors 27, 28 and corresponding spring elements. The spring elements delimit displacement in the direction of a force indicated by an arrow. FIG. 7 shows that the sensors 27, 28 and the spring elements thereof do not therefore have a separate sensor system, but are dimensioned such that actuation of the pushbutton 48 only results in minimal measured values of the force sensor 23, so that actuation of the pushbutton is always below a switching threshold for collision detection. The pushbutton is used as an operator control and is representative of a plurality of such operator controls. In addition, switches or a control panel (e.g., a touch-sensitive screen or a keypad) may be provided in the cover panel 26. Evaluation software may be used to process the signal obtained by the force sensor 23 in order to set the sensitivity of the force sensor 23 such that no triggering occurs during normal operation or in the event of actuation of the pushbutton 48.

If a higher switching threshold of the sensor values obtained by the force sensor 23 is exceeded, the corresponding drive of the moving component causing the collision is disconnected.

A further development of the exemplary embodiment shown in FIG. 7 provides that, in addition to the mechanical switching element, which is implemented as a pushbutton 48, another force measurement takes place (e.g., by a one-dimensional force sensor that is disposed under the pushbutton 48, such as inside the cover panel 26). Comparison of the two measured values makes it possible to differentiate between an operating force and an increased force possibly resulting from a collision. The central suspension of the paneling 26 at the sensor produces good signal quality, and the substructure (e.g., the base body) is simplified while preserving the multidimensional mechanical characteristics and also retaining the safety functionality.

Figure 8:
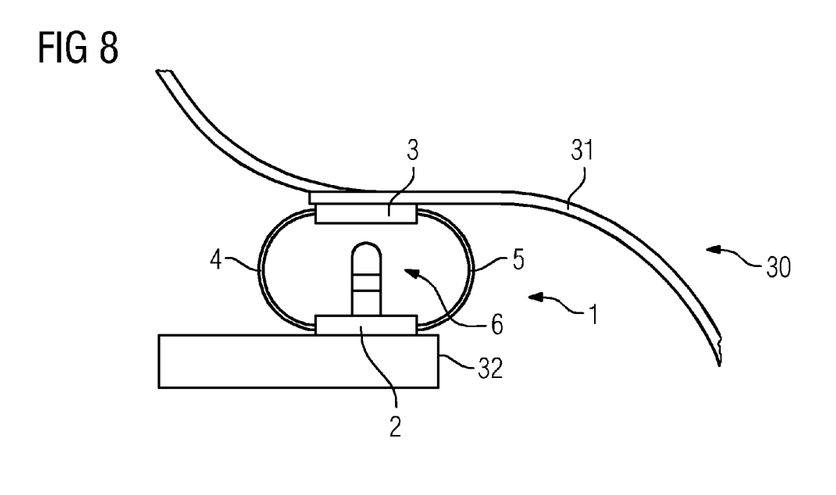
FIG. 8 schematically illustrates one embodiment of a sensor disposed on a medical examination and/or treatment device.

FIG. 8 is another exemplary embodiment and shows a detail of a medical examination and/or treatment device 30 having a cover panel 31 that is spaced apart from a base body 32. Disposed between the base body 32 and the cover panel 31 is a sensor 1. The first plate 2 of the sensor 1 is attached to the base body 32, and the second plate 3 of the sensor 1 is attached to the inside of the cover panel. The cover panel 31 is accordingly supported by the spring elements 4, 5 of the sensor 1. This allows simple placement of the spring elements 4, 5, as well as easy adjustment of the spring deflection and of the force counteracting the impact of any collision. Damage to the cover panel 31 is prevented by the modular insert 6 of the sensor 1 and corresponding components being configured such that deformations of the cover panel 1 occur exclusively in the elastic region.

Figure 9:
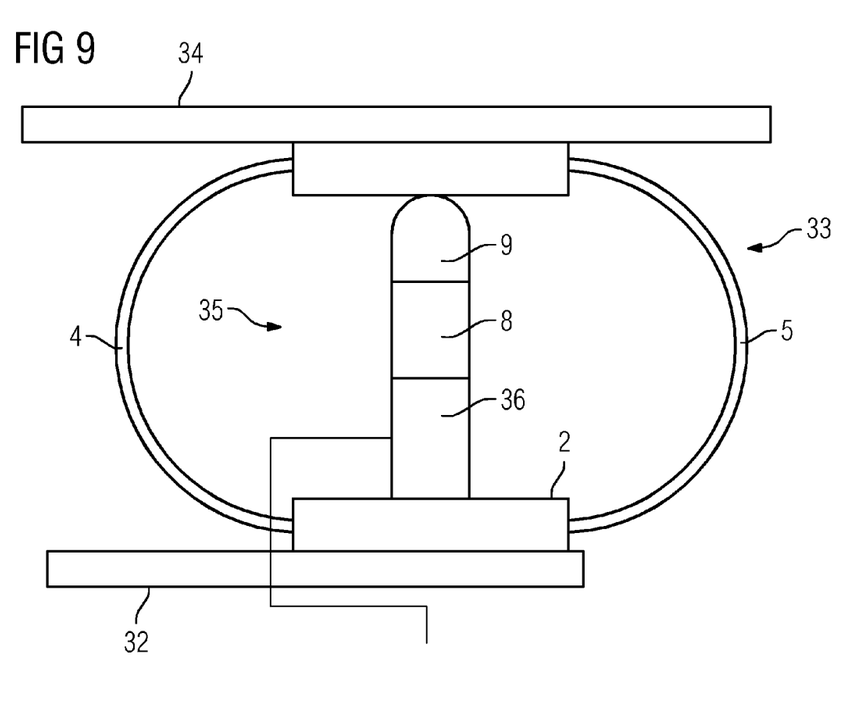
FIG. 9 schematically illustrates an exemplary embodiment of a sensor disposed under a cover panel.

FIG. 9 shows another exemplary embodiment of a sensor 33 having a lower plate 2 that is mounted on a base body 32. The sensor 33 also includes an upper plate 3 and spring elements 4, 5. The upper plate 3 is mounted on the inside of a cover panel 34. A modular insert 35 extends from the lower plate 2 to the opposite upper plate 3 spaced apart therefrom. The modular insert 35 includes a piezoelectric element 36, an elastic building block 8, and a hemispherically shaped building block 9. The elastic building block 8 produces the required compliance in the longitudinal direction of the modular insert 35. The hemispherically shaped building block 9 provides that torques are not blocked, and the piezoelectric building block 36 is configured to measure forces acting in the longitudinal direction. The sensor 33 is configured to produce restoring forces and torques in six degrees of freedom.

Figure 10:
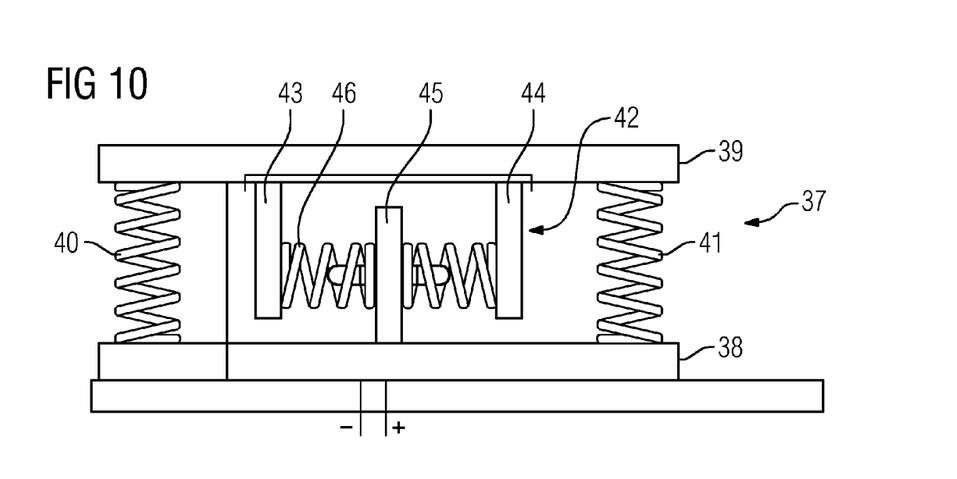
FIG. 10 schematically illustrates another exemplary embodiment of a sensor.

FIG. 10 is another exemplary embodiment and shows a sensor 37 having a lower plate 38 and an upper plate 39 that are disposed parallel to and spaced apart from one another and are made of a metal material. Accordingly, the two plates 38, 39 are electrically conductive. Extending between the two plates 38, 39 in the vertical direction are coil springs 40, 41 made of electrically nonconductive material. In the exemplary embodiment shown, the springs 40, 41 are made of a plastic material. Metal springs coated with a nonconductive material may also be used.

The plate 38 is connected to a first terminal (e.g., the positive terminal of a voltage source), and the plate 39 is connected to the other terminal (e.g., the negative terminal). Provided between the two springs 40, 41, which are disposed in the region of the side ends of the plates 38, 39, is a conductive insert 42 including two pins 43, 44 mounted on the upper plate 39 and extending vertically from the upper plate 39 to the opposite plate 38. Similarly, a pin 45 extends from the lower plate 38 to the plate 39. The pins 43, 44, 45 are spaced apart from the opposite plate in each case. Only in the event of an external compressive force causing the two plates 38, 39 to be moved onto one another do the nonattached ends of the pins 43, 44, 45 touch the opposite plate, causing a circuit to be completed. To control the stiffness or compliance, springs 46 are disposed transversely between the pins 43, 45 and the pins 44, 45 in each case. When the circuit is completed, a signal change occurs. The signal change is acquired and used to detect a collision.

Figure 11:
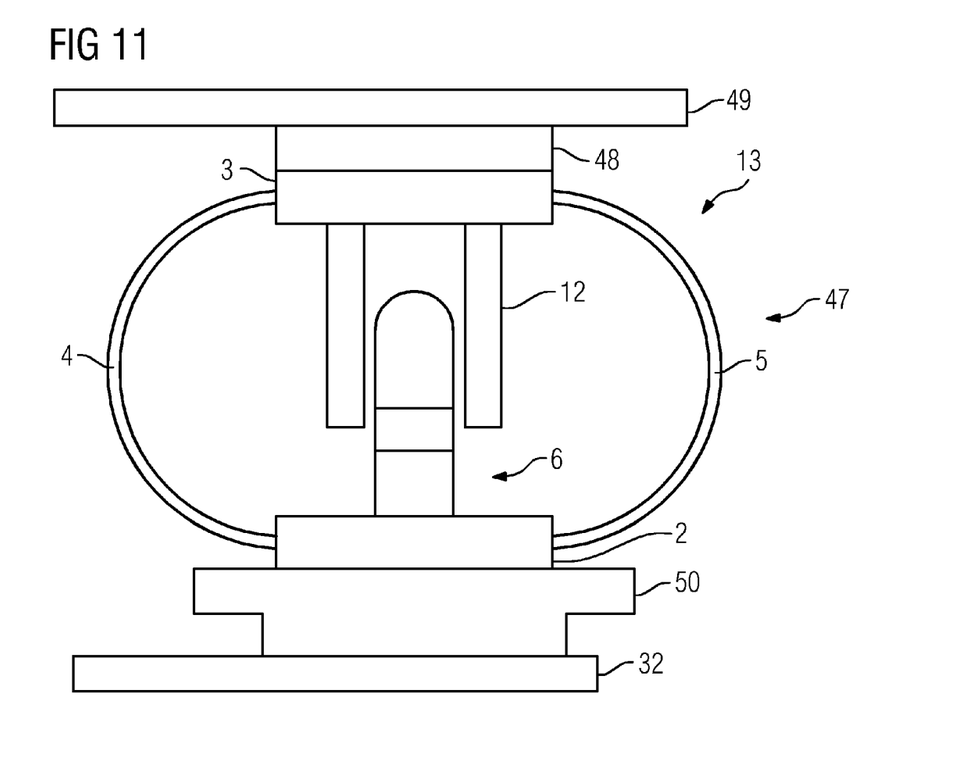
FIG. 11 schematically illustrates another exemplary embodiment of a sensor.

FIG. 11 is another exemplary embodiment and shows an arrangement 47 including the sensor 13 shown in FIG. 3. The sensor 13 includes the spring elements 4, 5, the modular insert 6, and the limiting element 12 implemented as a hollow cylinder. Disposed on the upper plate 3 is a mechanical switching element that is implemented as a pushbutton 48 and is mounted on the inside of a cover panel 49. Disposed under the plate 2 is a multiaxial sensor 50 that is attached to the base body 32. When an external force is applied, the switching element implemented as a pushbutton 48 is first actuated. The force may then be measured by the multiaxial sensor 50. This makes it possible to differentiate between an operating procedure in which the cover panel 49 is deliberately touched and an unwanted collision.

Although the invention has been illustrated and described in detail with reference to the exemplary embodiments, the invention is not limited by the examples disclosed. Other variations may be inferred therefrom by the average person skilled in the art without departing from the scope of protection sought for the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A medical examination, treatment, or examination and treatment device comprising:
   a cover panel comprising a sensor for detecting a collision, the sensor comprising:
      a first plate mounted on the medical examination, treatment, or examination and treatment device; and
      a second plate mounted on the inside of the cover panel and spaced apart from the first plate,
   wherein spring elements are disposed between the first plate and the second plate.

2. The medical examination, treatment, or examination and treatment device of claim 1, wherein the spring elements are made of a spring wire material or an elastomer.

3. The medical examination, treatment, or examination and treatment device of claim 1, wherein the spring elements are at least approximately semicircular and form a ring with the first plate and the second plate.

4. The medical examination, treatment, or examination and treatment device of claim 1, wherein the sensor further comprises at least one modular insert, the at least one modular insert comprising at least one component, the at least one component comprising a switching element, a gyrosensor, an elastically deformable building block, a hemispherically shaped building block, a metal or metal alloy building block, a piezoelectric element, or any combination thereof, wherein the at least one component is disposed on one plate of the first plate and the second plate.

5. The medical examination, treatment, or examination and treatment device of claim 4, wherein the at least one component of the at least one modular insert is columnar and extends from one plate of the first plate and the second plate to the other plate of the first plate and the second plate.

6. The medical examination, treatment, or examination and treatment device of claim 4, wherein the at least one component comprises a plurality of components, and
wherein the at least modular insert is assembled from the plurality of components as building blocks according to requirements.

7. The medical examination, treatment, or examination and treatment device of claim 4, wherein the at least one component comprises the hemispherically shaped building block, and
wherein the hemispherically shaped building block forms a nonattached end of the modular insert.

8. The medical examination, treatment, or examination and treatment device of claim 4, wherein the at least one modular insert comprises two modular inserts spaced apart from one another.

9. The medical examination, treatment, or examination and treatment device of claim 8, wherein one modular insert of the two modular inserts is assigned a limiting element disposed on the second plate.

10. The medical examination, treatment, or examination and treatment device of claim 9, wherein the limiting element is implemented as a hollow cylinder.

11. The medical examination, treatment, or examination and treatment device of claim 1, wherein one plate of the first plate and the second plate is a multiaxial force sensor or is implemented as a multiaxial force sensor.

12. The medical examination, treatment, or examination and treatment device of claim 11, wherein the multiaxial force sensor is disposed between two sensors disposed on opposite sides of the multiaxial force sensor and having spring elements.

13. The medical examination, treatment, or examination and treatment device of claim 11, wherein one plate of the first plate and the second plate has a switching element.

14. The medical examination, treatment, or examination and treatment device of claim 13, wherein the switching element comprises a pushbutton.

15. The medical examination, treatment, or examination and treatment device of claim 1, wherein the first plate and the second plate are electrically conductive, and
wherein at least one plate of the first plate and the second plate comprises at least one contact element extending to the other plate of the first plate and the second plate.

16. The medical examination, treatment, or examination and treatment device of claim 15, wherein the spring elements mounted between the first plate and the second plate are electrically nonconducting.

17. The medical examination, treatment, or examination and treatment device of claim 1, further comprising a multiaxially movable boom, the multiaxially movable boom comprising a C-arm, a cover panel of the C-arm being the cover panel comprising the sensor.

18. A medical system comprising:
a moveable arm for medical examination or treatment; and
a cover panel of the moveable arm, the cover panel comprising a sensor for detecting a collision, the sensor comprising:
a first plate mounted on the moveable arm;
a second plate mounted on the inside of the cover panel and spaced apart from the first plate; and
spring elements disposed between the first plate and the second plate.

* * * * *